(12) United States Patent
Abdou

(10) Patent No.: US 7,476,228 B2
(45) Date of Patent: Jan. 13, 2009

(54) DISTRACTION SCREW FOR SKELETAL SURGERY AND METHOD OF USE

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 200 days.

(21) Appl. No.: 10/683,325

(22) Filed: Oct. 10, 2003

(65) Prior Publication Data
US 2004/0133207 A1   Jul. 8, 2004

Related U.S. Application Data

(60) Provisional application No. 60/417,776, filed on Oct. 11, 2002.

(51) Int. Cl.
*A61B 17/58* (2006.01)
(52) U.S. Cl. .................. 606/104; 606/305; 606/300; 606/86 A; 606/286; 606/295; 606/323; 606/99; 81/453
(58) Field of Classification Search ............ 606/72, 606/73, 99, 65, 300–314, 318, 319–321, 606/325, 86 A, 281, 286–287, 289–291, 295–296, 606/326, 328, 907, 909, 916, 76–77, 323, 606/96, 104; 623/17.11; 411/389, 397, 401
See application file for complete search history.

(56) References Cited

U.S. PATENT DOCUMENTS 824,983 A * 7/1906 Harrington ............... 411/403

(Continued)

FOREIGN PATENT DOCUMENTS

EP         1180348        2/2002

(Continued)

OTHER PUBLICATIONS

The Effect of Cutting Flute Design on the Insertion and Pullout Properties of Self-tapping Bone Screws; Scott Yerby, Ph.D., C. Corey Scott, MS, Nathan J. Evans, MS, Katie L. Messing, MS, and Dennis R. Carter, Ph.D.; pp. 1-2; Jul. 2, 2002.

(Continued)

*Primary Examiner*—Eduardo C Robert
*Assistant Examiner*—James L Swiger, III
(74) *Attorney, Agent, or Firm*—Fred C. Hernandez; Mintz, Levin, Cohn, Ferris, Glovsky and Popeo P.C.

(57) ABSTRACT

An improved distraction bone screw and a method for its use are described. The distraction screw is comprised of an implantable distal segment and a detachably secured proximal segment. The distal segment includes a head portion and a threaded shank portion. The proximal segment is represented as an elongated body having an internal bore that extends through its length. A deployable member is disposed within the bore, which is extendible outside the internal bore to securely couple to the distal segment. As an assembly, the distraction screw is used to affix and realign bone during surgical reconstruction. Upon completion of the surgical work, the proximal segment is removed and the distal segment is left attached to the reconstructed bone. Securely affixed, the distal segment provides an additional point of fixation for the skeletal plates that are used to preserve the bony alignment while bone healing occurs. The affixed distal segment will also provide a ready mechanism for distraction screw replacement at the time of surgical revision without obligatory plate removal. Different embodiments of the proximal segment, distal segment and the rotational locking mechanisms which inhibit the rotation of one segment relative to the other during deployment were also described. In addition, in cases where the distraction screw must be placed into the bone at an inclined angle, poly-axial heads were provided so that proper skeletal plate placement can still be accomplished.

42 Claims, 9 Drawing Sheets

U.S. PATENT DOCUMENTS

| | | | |
|---|---|---|---|
| 2,248,054 A * | 7/1941 | Becker | 81/457 |
| 2,329,398 A * | 9/1943 | Duffy | 606/104 |
| 2,370,407 A * | 2/1945 | McCartney | 81/453 |
| 2,574,352 A * | 11/1951 | Senter | 81/125 |
| 3,236,141 A * | 2/1966 | Smith | 269/48.3 |
| 3,604,487 A * | 9/1971 | Gilbert | 81/443 |
| 3,659,595 A | 5/1972 | Haboush | |
| 4,399,813 A * | 8/1983 | Barber | 606/99 |
| 4,877,020 A * | 10/1989 | Vich | 606/86 R |
| 4,903,692 A * | 2/1990 | Reese | 606/99 |
| 5,252,016 A * | 10/1993 | Schmid et al. | 411/386 |
| 5,275,601 A * | 1/1994 | Gogolewski et al. | 606/72 |
| 5,352,231 A * | 10/1994 | Brumfield et al. | 606/99 |
| 5,354,292 A * | 10/1994 | Braeuer et al. | 606/1 |
| 5,360,429 A | 11/1994 | Jeanson et al. | |
| 5,439,339 A * | 8/1995 | Batchelor | 411/407 |
| 5,484,440 A * | 1/1996 | Allard | 606/73 |
| 5,487,742 A | 1/1996 | Cotrel | |
| 5,531,747 A | 7/1996 | Ray | |
| 5,534,001 A * | 7/1996 | Schlapfer et al. | 606/302 |
| 5,534,027 A * | 7/1996 | Hodorek | 128/898 |
| 5,545,164 A | 8/1996 | Howland | |
| 5,558,674 A | 9/1996 | Heggeness et al. | |
| 5,591,166 A * | 1/1997 | Bernhardt et al. | 606/61 |
| 5,607,426 A * | 3/1997 | Ralph et al. | 606/287 |
| 5,616,142 A | 4/1997 | Yuan | |
| 5,649,931 A * | 7/1997 | Bryant et al. | 606/104 |
| 5,672,176 A | 9/1997 | Biedermann et al. | |
| 5,681,311 A | 10/1997 | Foley | |
| 5,681,312 A | 10/1997 | Yuan et al. | |
| 5,681,313 A | 10/1997 | Diez | |
| 5,704,936 A | 1/1998 | Mazel | |
| 5,707,372 A | 1/1998 | Errico et al. | |
| 5,709,686 A | 1/1998 | Talos et al. | |
| 5,713,900 A | 2/1998 | Benzel et al. | |
| 5,716,357 A | 2/1998 | Rogozinski | |
| 5,735,853 A * | 4/1998 | Olerud | 606/71 |
| 5,876,402 A * | 3/1999 | Errico et al. | 606/287 |
| 5,904,683 A | 5/1999 | Pohndorf et al. | |
| 5,954,722 A | 9/1999 | Bono | |
| 5,964,763 A | 10/1999 | Incavo et al. | |
| 5,971,987 A | 10/1999 | Huxel et al. | |
| 5,976,140 A * | 11/1999 | Haas | 606/328 |
| 5,993,449 A | 11/1999 | Schlapfer et al. | |
| 6,033,170 A * | 3/2000 | Gold | 411/480 |
| 6,059,786 A * | 5/2000 | Jackson | 606/73 |
| 6,117,135 A | 9/2000 | Schlapfer | |
| 6,139,316 A | 10/2000 | Sachdeva et al. | |
| 6,139,549 A | 10/2000 | Keller | |
| 6,187,005 B1 * | 2/2001 | Brace et al. | 606/264 |
| 6,251,112 B1 * | 6/2001 | Jackson | 606/916 |
| 6,306,136 B1 | 10/2001 | Baccelli | |
| 6,309,391 B1 | 10/2001 | Crandall et al. | |
| 6,331,179 B1 * | 12/2001 | Freid et al. | 606/61 |
| 6,361,258 B1 * | 3/2002 | Heesch | 411/178 |
| 6,402,752 B2 | 6/2002 | Schaffler-Wachter et al. | 606/61 |
| 6,402,756 B1 | 6/2002 | Ralph et al. | |
| 6,599,290 B2 * | 7/2003 | Bailey et al. | 606/69 |
| 6,645,207 B2 | 11/2003 | Dixon et al. | |
| 6,663,631 B2 | 12/2003 | Kuntz | |
| 6,666,867 B2 | 12/2003 | Ralph et al. | |
| 6,679,883 B2 * | 1/2004 | Hawkes et al. | 606/279 |
| 6,723,100 B2 * | 4/2004 | Biedermann et al. | 606/308 |
| 6,827,722 B1 * | 12/2004 | Schoenefeld | 606/104 |
| 6,830,571 B2 | 12/2004 | Lenke et al. | |
| 6,855,147 B2 | 2/2005 | Harrington, Jr. | |
| 6,979,334 B2 * | 12/2005 | Dalton | 606/287 |
| 2002/0016595 A1 * | 2/2002 | Michelson | 606/73 |
| 2002/0055741 A1 | 5/2002 | Schlapfer et al. | |
| 2002/0099386 A1 * | 7/2002 | Beger et al. | 606/104 |
| 2002/0111628 A1 * | 8/2002 | Ralph et al. | 606/61 |
| 2002/0143328 A1 | 10/2002 | Shluzas et al. | |
| 2002/0169453 A1 * | 11/2002 | Berger | 606/73 |
| 2002/0183755 A1 | 12/2002 | Michelson | |
| 2002/0188296 A1 | 12/2002 | Michelson | |
| 2003/0078583 A1 | 4/2003 | Biedermann et al. | |
| 2003/0153913 A1 | 8/2003 | Altarac et al. | |
| 2004/0204713 A1 | 10/2004 | Abdou | |
| 2004/0249380 A1 * | 12/2004 | Glascott | 606/73 |
| 2005/0004573 A1 | 1/2005 | Abdou | |
| 2005/0177163 A1 | 8/2005 | Abdou | |
| 2005/0273120 A1 | 12/2005 | Abdou | |
| 2005/0288669 A1 | 12/2005 | Abdou | |
| 2006/0074488 A1 | 4/2006 | Abdou | |
| 2006/0149278 A1 | 7/2006 | Abdou | |
| 2006/0217710 A1 | 9/2006 | Abdou | |
| 2006/0229615 A1 | 10/2006 | Abdou | |
| 2007/0093828 A1 | 4/2007 | Abdou | |
| 2007/0106383 A1 | 5/2007 | Abdou | |
| 2007/0123884 A1 | 5/2007 | Abdou | |

FOREIGN PATENT DOCUMENTS

| | | |
|---|---|---|
| FR | 2781359 | 1/2000 |
| WO | WO 2004/032726 | 4/2004 |
| WO | WO 2004/062482 | 7/2004 |
| WO | WO 2004/093702 | 11/2004 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

OTHER PUBLICATIONS

Day Surgery for Anterior Cervical Microdiskectomy: Experience with 75 Cases, Richard N.W. Wohns, M.D. and Roger D. Robinett, M.D., pp. 1-3, Jul. 11, 2002.

Derwent English Abstract for French Patent Publication FR 2781359, published Jan. 28, 2000, entitled: "Osteosynthesis frame for spinal surgery has rod with clamps to hold cross bars with anchor screws". Accession No. 9867555.

* cited by examiner

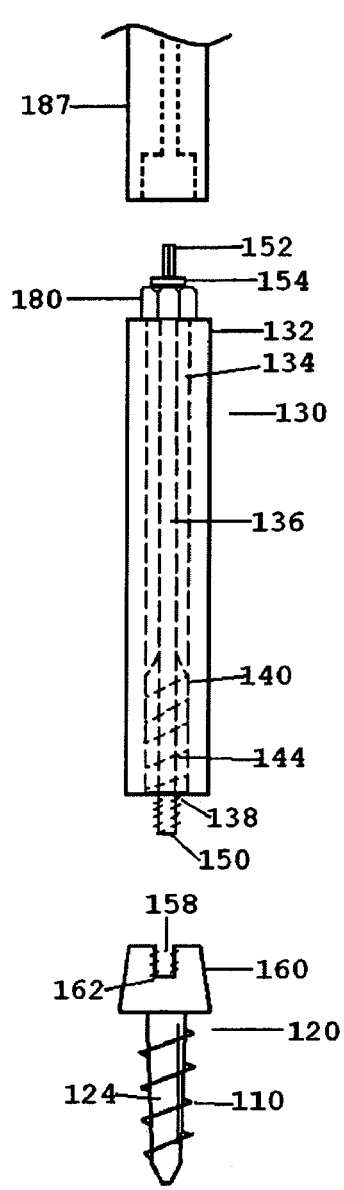
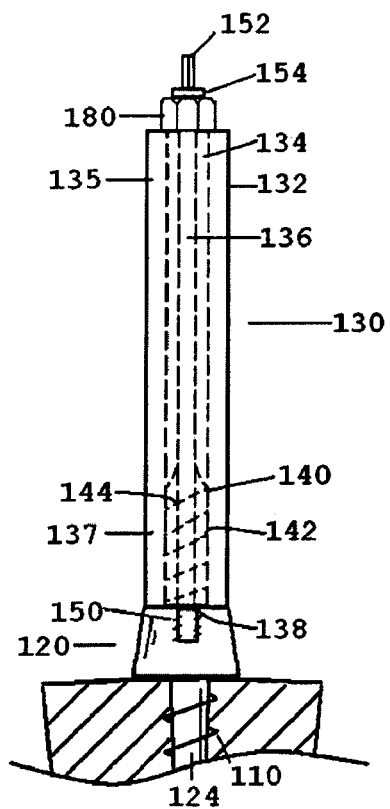
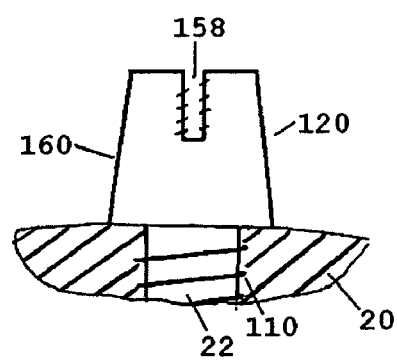
Fig. 1
Fig. 2
Fig. 3

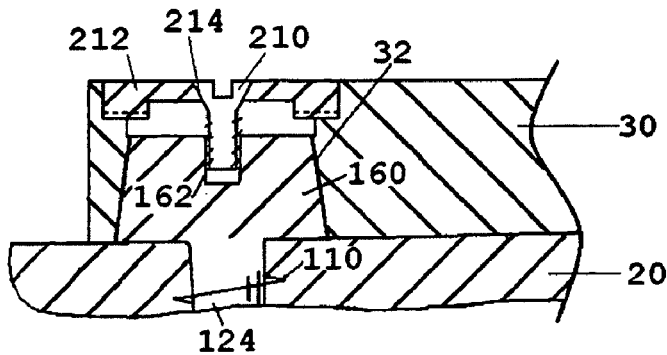
Fig. 4
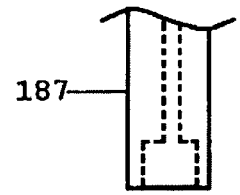
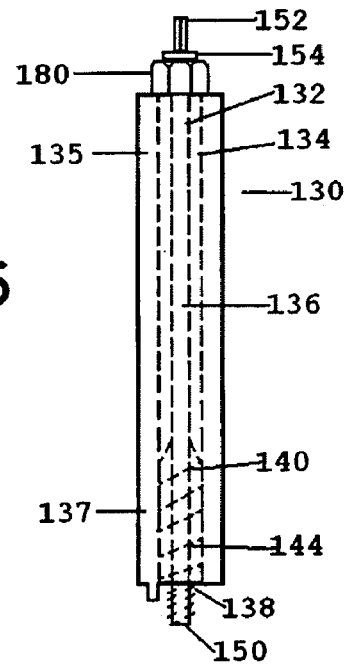
Fig. 5
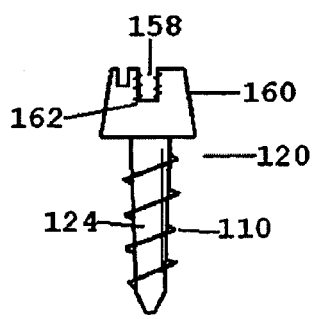

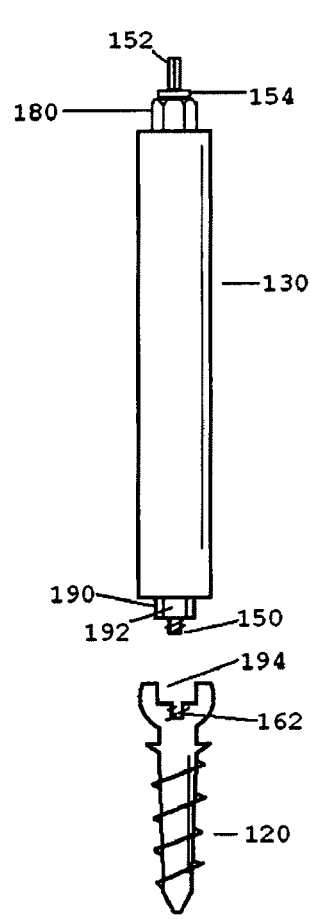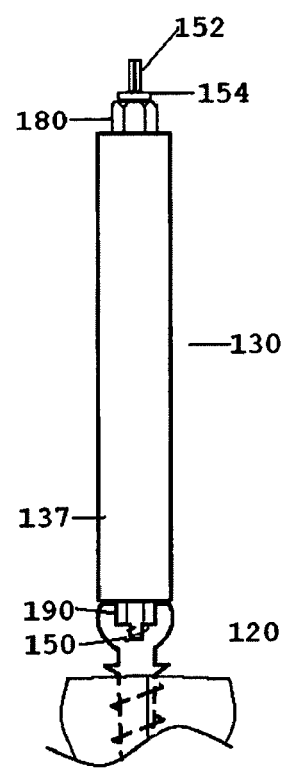
Fig. 6a
Fig. 6b

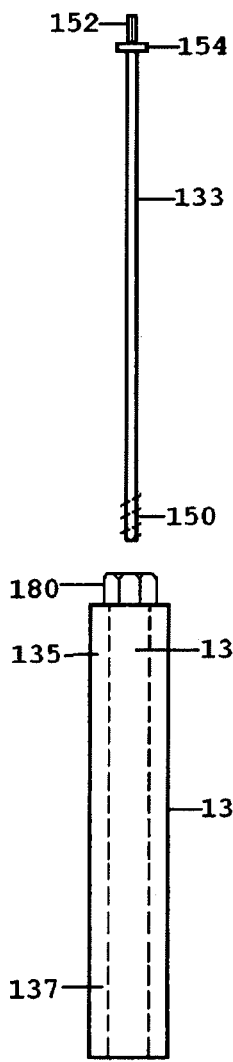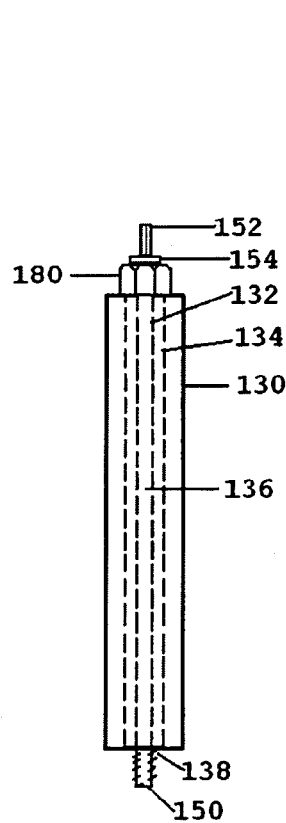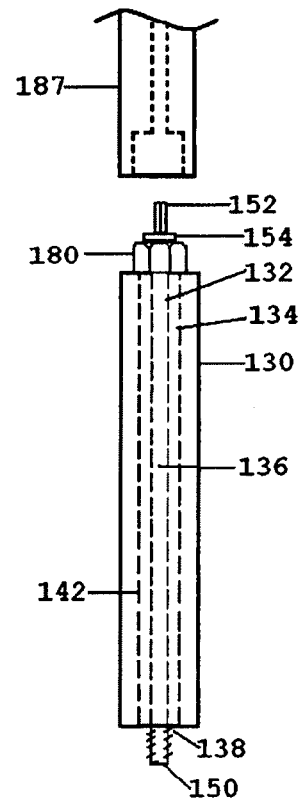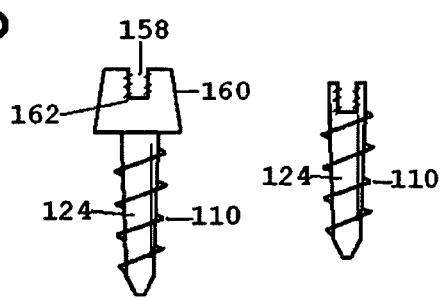
Fig. 7a
Fig. 7b
Fig. 7c

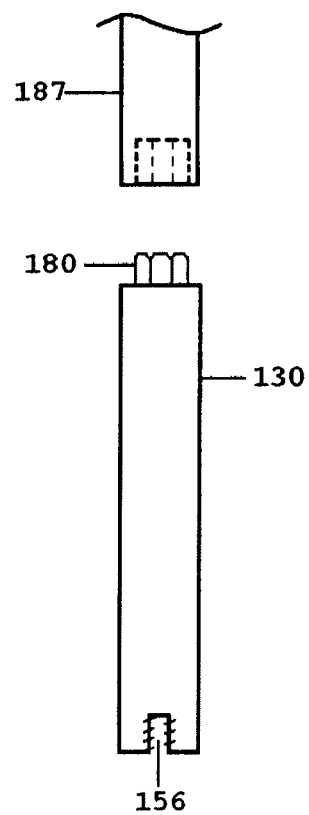
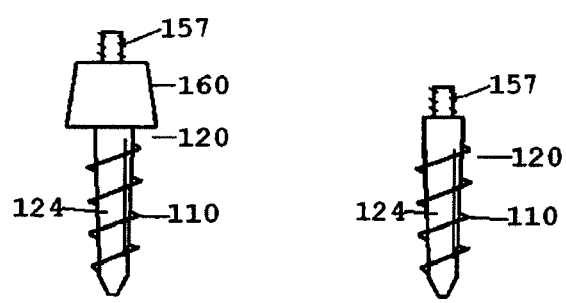
Fig. 8a
Fig. 8b    Fig. 8c

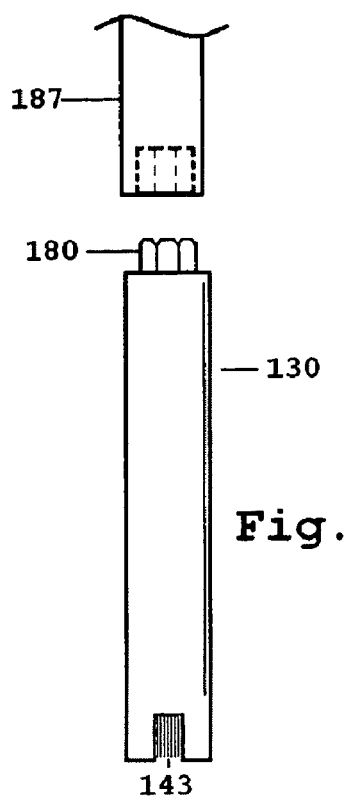
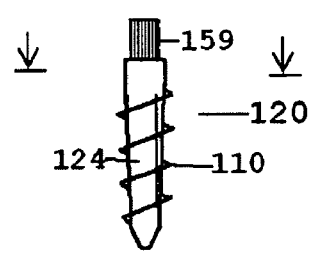
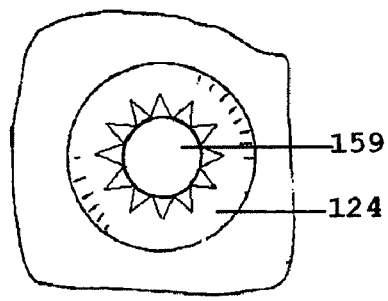
Fig. 9a
Fig. 9b
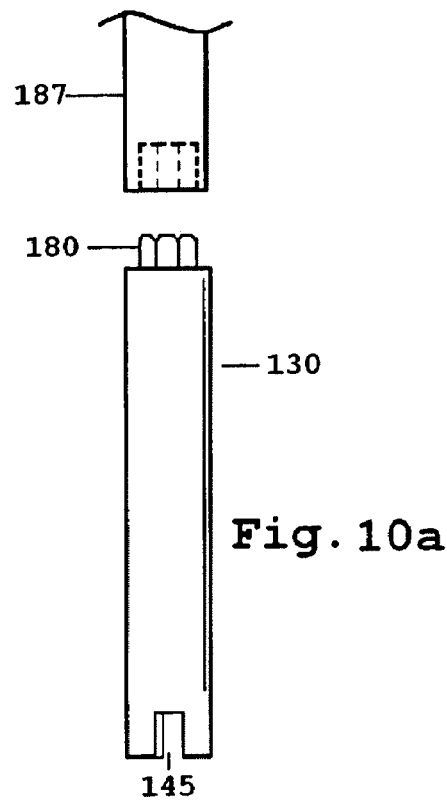
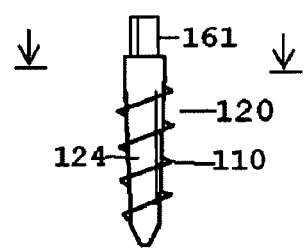
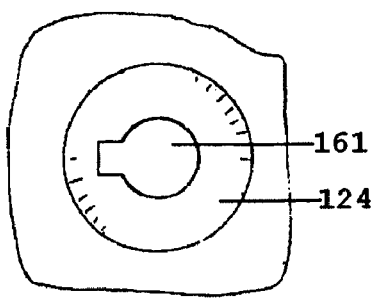
Fig. 10a
Fig. 10b

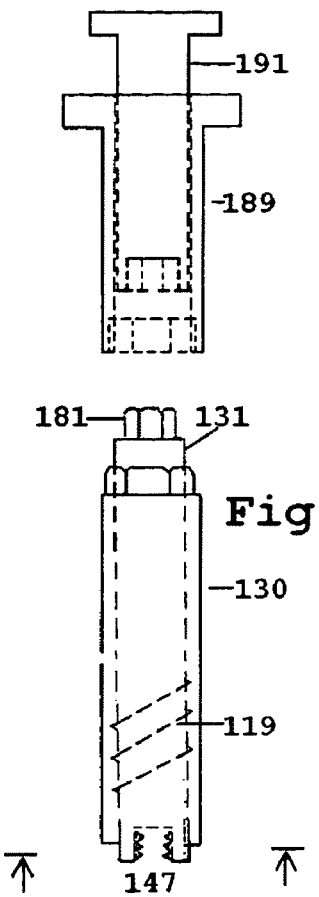
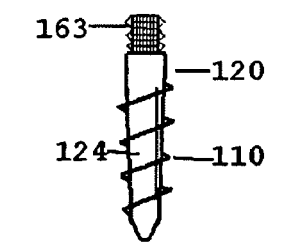
Fig. 11a
Fig. 11b.
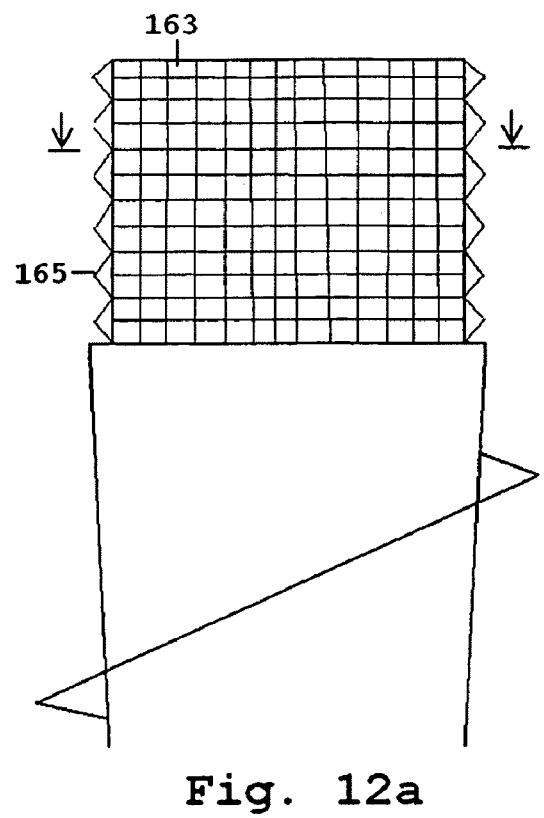
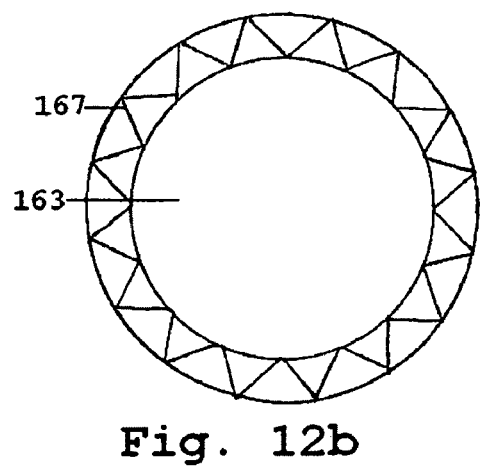
Fig. 12a
Fig. 12b

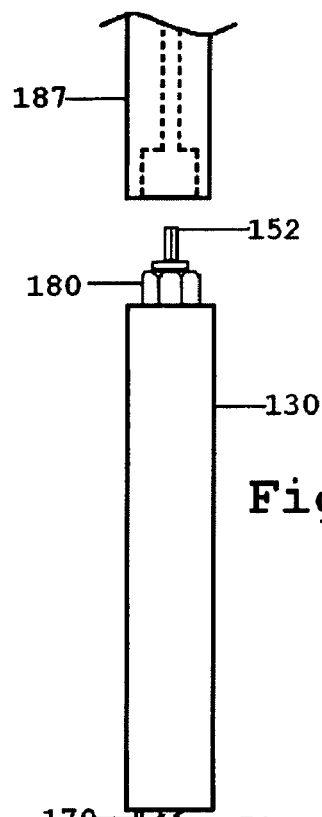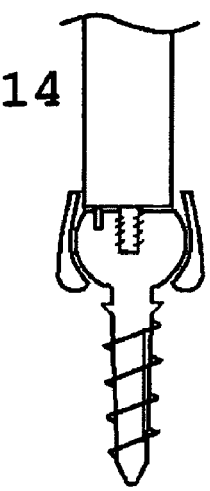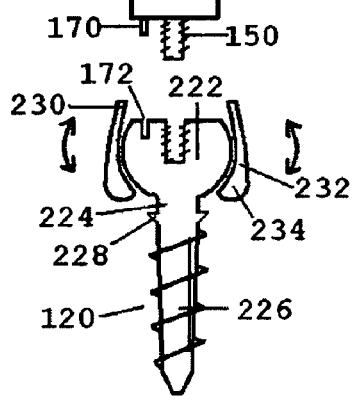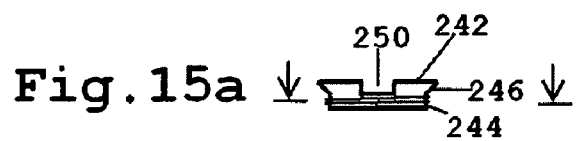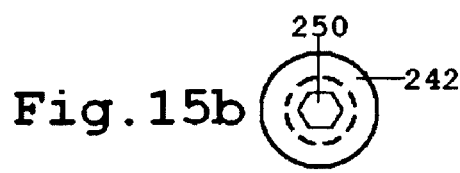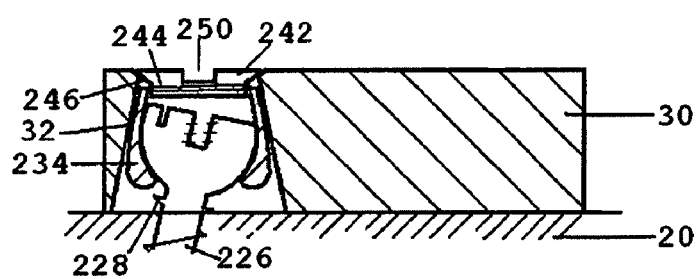

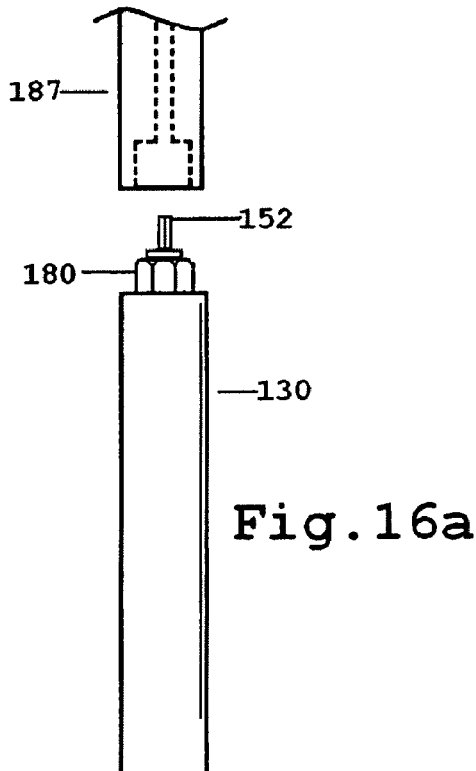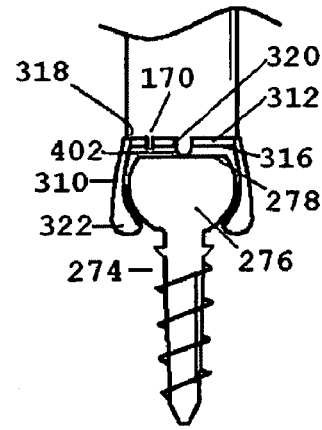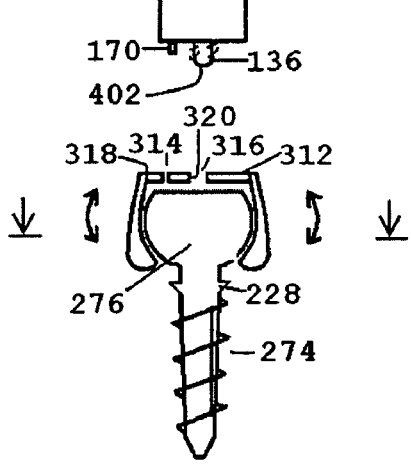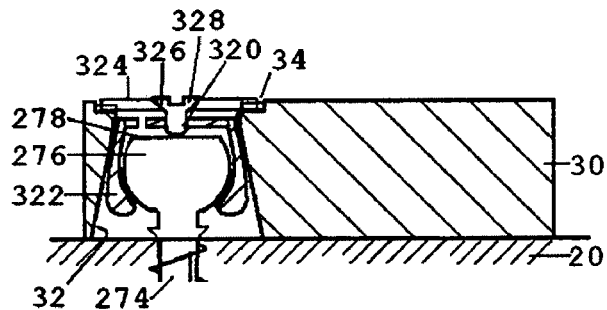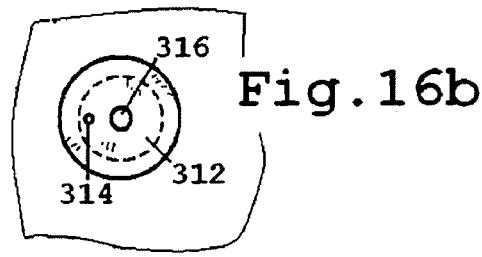

DISTRACTION SCREW FOR SKELETAL SURGERY AND METHOD OF USE

CROSS REFERENCE TO RELATED APPLICATION

This application claims the benefit of the U.S. Provisional Application No. 60/417,776 filed Oct. 11, 2002.

FIELD OF THE INVENTION

The present invention relates generally to skeletal plating systems and components thereof, which can be used to adjust, align and maintain the spatial relationship(s) of adjacent bones or bony fragments during healing and fusion after surgical reconstruction of a mammalian bone structure. Such systems can comprise skeletal plates, bone screws and/or distraction screws and plate-to-screw locking mechanisms.

BACKGROUND OF THE INVENTION

The surgical removal of a herniated disc, whether from degenerative disease or traumatic disruption, is a common procedure in current medical practice. In the cervical spine, the procedure involves placement of a large temporary bone screw, which is also known as the distraction screw, into each of the vertebral bones above and below the diseased disc space. These screws are used to realign the vertebral bones into the desired anatomical relationship and to temporarily distract them so as to permit work within the intervening disc space. The disc is removed and a bone graft or suitable graft substitute is placed into the evacuated space. The temporary distraction screws are then removed from the vertebrae and a metallic skeletal plate is used to maintain the position of the vertebral bones while bone healing occurs. The bones are fixed to the skeletal plate using implantable bone screws (usually two screws per vertebrae), which are separate and distinct from the distraction screws.

Removal of the distraction screws from the vertebral bodies usually produces robust bone bleeding and requires that the bone holes be filled with a hemostatic agent. The empty bone holes also act as stress concentration points within the vertebral bodies, as would any empty opening or crack within a rigid structural member, and predispose the vertebral bodies to bone fracture, screw/plate migration and construct failure. Further, the empty holes often interfere with proper placement of the implantable screws and the associated skeletal plate, making proper alignment of the plate along the anatomically desired plane more difficult. This is especially problematic since the plate is placed at the end of the operative procedure and the preceding surgical steps have distorted the anatomical landmarks required to ensure proper plate alignment.

Lastly, once placed, the plate will effectively cover the vertebral bodies of the reconstructed segment. Extension of the operation to an adjacent level at a future date will require placement of a distraction screw within a covered vertebra and, thus, necessitate plate removal. The latter requires re-dissection through the scarred operative field of the initial procedure and significantly increases the operative risk of the second procedure for the patient.

In view of the above, it would be desirable to design an improved distraction screw. The new device should minimize blood loss, reduce the potential for stress concentration, maximize the likelihood of proper plate alignment, provide an additional point of fixation for the skeletal plate and provide a ready mechanism for distraction screw replacement at the time of surgical revision without obligatory plate removal.

SUMMARY OF THE INVENTION

The present invention is one of an improved distraction screw and a method for its use. The design substantially enhances the functional capability of distraction screws used in the surgical reconstruction of mammalian bones. In this invention, the multi-segmental distraction screw comprises an implantable distal segment and a detachably secured proximal segment. The distal segment includes a head portion and a threaded shank portion. The proximal segment is represented as an elongated body having an internal bore that extends through its length. A deployable member is disposed within the proximal segment, which is extendable beyond the distal end of the internal bore to engage and secure the distal segment, thus forming a unitary distraction screw. Once assembled, the screw is used to realign and distract the bones during surgical reconstruction of a degenerated skeletal segment. Upon completion of that work, the proximal and distal segments are disengaged leaving the latter attached to bone. Securely affixed, the distal segment provides an additional point of anchoring and/or fixation for the skeletal plate and facilitates its proper placement. It also provides a ready mechanism for distraction screw replacement at the time of surgical revision without obligatory plate removal.

In other embodiments of the present invention, different proximal and distal segment designs are provided as well as an optional rotational locking means to inhibit the rotational movement of the proximal and distal segments relative to each other. Further, where the distal segment is affixed to the underlying bone at an inclined angle, a poly-axial head adapter is provided to ensure proper alignment during placement of the skeletal plate.

The distraction screw design of the present invention provides significant advantages over the current and prior art. These and other features of the present invention will become more apparent from the following description of the embodiments and certain modifications thereof when taken with the accompanying drawings.

BRIEF DESCRIPTION OF THE DRAWINGS

FIG. 1 is a partial side view of a distraction screw of the present invention, together with a tool driver to effect a rotational movement therefore;

FIG. 2 is a partial sectional side view of an assembled distraction screw of the present invention affixed onto a mammalian bone substrate;

FIG. 3 is a partial sectional side view of a distal segment of the distraction screw implanted onto a mammalian bone substrate;

FIG. 4 is a sectional side view of the distal segment affixing a skeletal plate onto the mammalian bone substrate;

FIG. 5 is a partial sectional side view of another embodiment of the present invention, which incorporates a rotational locking means as represented by a key-receptacle arrangement;

FIG. 6a is a partial sectional side view of a further embodiment of the present invention, which incorporates another variation of a rotational locking means as represented by a hex insert-socket arrangement;

FIG. 6b is a partial sectional side view of the assembled distraction screw shown in FIG. 6a affixed onto a mammalian bone substrate;

FIG. 7a is a sectional side view of another embodiment of the proximal segment;

FIG. 7b is a sectional side view of the assembled proximal segment shown in FIG. 7a;

FIG. 7c is a sectional side view of the assembled proximal segment shown in FIG. 7a, together with the distal segments and a tool driver to effect the rotational movement thereof;

FIG. 8a is a partial sectional side view of another embodiment of the proximal segment, together with a tool driver used to effect its rotation;

FIG. 8b is a sectional side view of one embodiment of the distal segment used with the proximal segment shown in FIG. 8a;

FIG. 8c is a sectional side view of another embodiment of the distal segment used with the proximal segment shown in FIG. 8a;

FIG. 9a is a partial sectional side view of another embodiment of the proximal and distal segments, together with a tool driver used to effect their rotation;

FIG. 9b is a top view of the distal segment illustrated in FIG. 9a;

FIG. 10a is a partial sectional side view of another embodiment of the proximal and distal segments, together with a tool driver used to effect their rotation;

FIG. 10b is a top view of the distal segment illustrated in FIG. 10a;

FIG. 11a is a partial sectional side view of another embodiment of the proximal and distal segments, together with a tool driver used to effect their rotation;

FIG. 11b is a partial top view of the distal segment illustrated in FIG. 11a;

FIG. 12a is a partial sectional side view of the distal segment of the embodiment illustrated in FIG. 11a;

FIG. 12b is a partial top view of the distal segment of the embodiment illustrated in FIG. 11a;

FIG. 13 is a partial sectional side view of another embodiment of the present invention, which incorporates a poly-axial feature;

FIG. 14 is a partial sectional side view of the embodiment of FIG. 13 shown as an assembly;

FIG. 15 is a partial sectional side view of a distal segment with a poly-axial feature implanted onto a mammalian bone substrate on which a skeletal plate is affixed;

FIG. 15a is a partial top view of a mounting plate used to secure the skeletal plate onto the distal segment;

FIG. 15b is a side view of the mounting plate of FIG. 15a;

FIG. 16a is a partial sectional side view of another embodiment of the present invention incorporating another variation of the poly-axial feature;

FIG. 16b is a top view of the screw cap shown in FIG. 16a;

FIG. 17 is a partial sectional side view of the assembled distraction screw of the embodiment shown in FIG. 16a; and FIG. 18 is a partial sectional side view of a distal segment with poly-axial feature implanted onto a mammalian bone substrate on which a skeletal plate is affixed.

DETAILED DESCRIPTION

The present invention provides an improved distraction screw and a method for its use. FIG. 1 shows an embodiment of the present invention, as represented by a distraction screw 10, which comprises a distal segment 120 and a removable proximal 130 segment. The distal segment 120 is implantable on a vertebral bone as part of the surgical procedure. The distal segment 120 has a head portion 122, and a threaded shank portion 124 which can be securely fastened unto the bone structure and which may be self-tapping and/or self-drilling.

As shown in FIGS. 1 and 2, the proximal segment 130 has an elongated body 132 with an internal bore 134 extending through its length from its proximal end portion 135 to its distal end portion 137. The elongated body 132 houses a deployable member 136, which is disposed within the internal bore 134. The deployable member 136 is adapted to be retractably deployed beyond the opening 138 of the internal bore 134 at the distal end portion 137 of the elongated body 132.

Along the wall 140 of the interior bore 134 of the elongated body 132 are cooperating threads 142, which complement threads 144 of the deployable member 136 such that rotation of the deployable member 136 relative to the elongated body 132 in one direction extends it beyond the opening 138 of the internal bore 134 in a deployed position, as shown in FIGS. 1 and 2. Conversely, rotation of the deployable member 136 in the opposite direction effects its retraction from the deployed position. Thus the deployable member 136 can be rotated independently of the elongated member 130.

For the embodiment shown in FIG. 1, the threads are made as right-hand thread, that is, viewing from the proximal end portion 135 of the elongated body 132, a clockwise rotation of deployable member 136 causes it to extend beyond the opening 138 of the internal bore 134. Conversely, a counter-clockwise rotation of the deployable member 136 effects its retraction into the internal bore 134.

The proximal segment 130 is adapted to be attached to the distal segment 120. As shown in FIGS. 1 and 2, the deployable member 136 has a threaded end portion 138, with threads 150, which are adaptably securable to interfit and interlock with complemental threads 162 of the threaded well 158 of the distal segment 120. Threads 150 and 162 are oriented in the same turn direction and have the same pitch (number of threads per unit length) as those of threads 142 and 144. This enables the threaded portion 138 to advance into the threaded well 158 when turned clockwise.

Construction of the threads 142 and 150, and their respective counterpart complemental threads 144 and 162 can be accomplished by various means. For example, threads 142 and 144 can be constructed as a screw drive arrangement to facilitate the relative movement between the elongated body 132 and the deployable member 136 in deployment or retraction. Likewise, threads 150 and 162 can be constructed for effective mutual engagement. As a matter of design preference, threads 142 and 144 may be of any length and may be placed at any point throughout the internal bore of the elongated member. In addition, though not necessary, threads 150 of the deployable member 136 can be an extension of its threads 144.

At its proximal end portion 152, the deployable member 136 is adapted to be manipulated to effect its extension beyond the opening 138 of the internal bore 134 in a deployed position or retraction. For the embodiment as shown in FIGS. 1 and 2, the rotational movement of the deployable member 136 can be effected by tools such as a wrench, socket wrench, screwdriver, or the like. In one embodiment of the present invention as shown in FIG. 1, the proximal end portion 152 of the deployable member 136 has a hex-shaped configuration, which is engageable by a socket or a wrench to effect a rotational action. In alternative embodiments, proximal end portion 152 has an intersecting depression (not shown) adapted to accommodate the driving tip of a "Phillips" screwdriver to effect a rotational action. Any alternative means and arrangements for engaging and rotating the deployable member 136 can be employed including, but not limited to, a driver or "Allen" wrench configuration.

As referenced above, rotation of the deployable member 136 relative to the elongated body 130 extends the deployable member for its threads 150 to engage the threads 162 of the head portion 160 of the distal segment 120. Once threads 150 are engaged with threads 162, both the proximal and the distal segments are coupled as a unit.

The deployable member 136 can be removed from the elongated body 132, allowing for different sizes, threads and/or shapes for the head portion and/or tool attachment portions. Thus, the attachment and/or arrangement of the elongated body 132 and the deployable member 136 can be a screw-fit, or snap-fit arrangement, which does not interfere with the rotation of the deployable member 136.

The proximal segment 130 is provided with a tool attachment end portion 180 that is adaptable to receive a rotational torque to effect a rotational action of the elongated body 132. As shown in FIG. 1, a "hex-head" end configuration is provided, on which a socket 187 can be fitted to effect the rotational action of the elongated body 132. Optionally, the proximal end can incorporate a flange 154 to limit the extension of the deployable member 136 beyond the distal end of the proximal segment.

The coupled proximal and distal segments employing the above-described means of engagement provide a detachably coupled distraction screw, which functions as a unitary device. In a surgical application, a socket (coupled to a wrench, not shown) 187 is attached to the tool attachment portion 180, and the distraction screw is positioned at a site of a bone structure 20. By applying a rotational torque to the elongated body 132 in a clockwise direction, both the proximal and distal segments rotate in unison so that thread 110 of the distal segment 120 may engage opening 22 of the underlying bone. Shank 124 is advanced and secured onto the bone structure as shown in FIG. 2.

As shown in FIGS. 1 and 2, the distal segment 120 comprises a threaded shank portion 124 and a head portion 160. As referenced above, threads 110 of the shank portion 124 would preferably, but not necessarily, be self-tapping and/or self-drilling. The threads 110 would also follow the same turn direction as those of threads 150 and 144. Depending on the particular application, the shank portion 124 can be of variable lengths and threads 110 may be of any known configurations. One of ordinary skill in the art would understand that the threads can be of any design that is understood and well known to be applicable for screwing and inserting into mammalian bone. In the embodiment shown in FIGS. 1, 2 and 3, the internal diameter of the threaded shank portion is progressively tapered from the head portion to the distal tip.

The shape of the head portion 160 may be of any geometric design, including but not limited to, rectangular, trapezoidal, cylindrical, circular, spherical, hybrid configurations and the like. Further, the head may be absent altogether, placing the engagement adapter directly into the body of the screw shank (FIG. 7c). In the embodiment as shown in FIGS. 1, 2 and 3, the head portion 160 is mono-axial, remaining in a fixed plane relative to the threaded shank. As used herein, "mono-axial" refers to rotation of the head portion and shank along a common arbitrary axis. This is defined by the placement of the head portion in a fixed geometric relationship to the threaded shank such that when the shank is rotated, the head portion also rotates along the same axis. Thus, in the embodiment as shown in FIGS. 1, 2 and 3, the head portion is arranged with its diameter perpendicular to the length of the shank, which defines a common mono-axial relationship.

The distal segment 120 can be made of any biologically adaptable or compatible materials. Materials considered acceptable for biological implantation are well known and include, but are not limited to, stainless steel, titanium, combination metallic alloys and the like, various plastics, ceramics, biologically absorbable materials and the like. It would be understood by one of ordinary skill in the art that the distal segment 120 can be made of any materials acceptable for biological implantation and capable of withstanding the torque required for insertion and the load encountered during use. Any components may be further coated/made with osteoconductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. The proximal segment 130 may be made from any non-toxic material capable of withstanding the torque required for insertion and the load encountered during use. Materials used in the proximal segment 130 need not be limited to those acceptable for implantation, since it functions to deliver the implatable distal segment 120 but is not, itself, implanted.

As shown in FIG. 2, the distraction screw 10 is placed at a predefined location of the vertebral bone. As rotational torque is applied to the distal segment 120 by the tool attachment, both the segments rotate in unison, which inserts the threaded portion 110 of the distal segment into the bone opening 22. The coupling of the proximal and distal segments provides the longitudinal stability and the structural integrity of the coupled segments as a distraction device. In another embodiment of the present invention as shown in FIGS. 5, 6a and 6b, in addition to coupling the deployable member 136 with the distal segment 120, the elongated body 132 of the proximal segment 130 is also engageable to the distal segment 120 to prevent their relative rotational movement by a rotation locking means.

As shown in FIG. 5, at the distal end portion 137 of the proximal segment 130, a key 170 is provided. The key 170 is fitted to be inserted into a receptacle 172 as defined by a depression located at the head portion 160 of the distal segment 120. When the key 170 is inserted into receptacle 172, the elongated body 132 of the proximal segment 130 is engaged with the distal segment 120, which prevents the relative rotational movement between the two segments. FIGS. 6a and 6b show another embodiment of the present invention in which a variation in the design of the rotation locking means is presented. The distal end portion 137 of the proximal segment 130 incorporates a hex extension 190, which can be fitted into the well 158 of the head portion 160 with a complemental hex socket receptacle 194. When so fitted, rotation of the distal segment 120 proximal segment 130 relative to each other is inhibited. As shown in FIGS. 6a and 6b, hex extension 190 has an internal bore 192 through which the deployable member 150 passes for engagement with the distal segment by way of their cooperating threads 150 and 162.

While the rotation locking means is illustrated in a key-receptacle arrangement and hex extension-socket configuration, it is not limited to these examples. It is understood that any engageable arrangement can be used as a rotational locking means. These include, but are not limited to, one or more extended protuberances of the elongated body 132 to seat within complemental bored depressions on the head portion of the distal segment 120. Similarly, square-jaw or spinal jaw clutch arrangements, and serrated or saw tooth edges can be incorporated to mate or interlock with similar features on the head portion (not shown).

In embodiments that incorporate such rotation locking means, assembly of the proximal and distal segments can be easily accomplished. The deployable member 136 is fitted within the internal bore 134 of the elongated body 132 in a retracted configuration by effecting a relative rotational movement between elongated body and the deployable member along their cooperating threads. The proximal segment 130 is then held adjacent to the head portion 160 of the distal segment 120 to insert key 170 into the receptacle 172. For the embodiment shown in FIGS. 6a and 6b, the hex extension 190 is seated within the socket 194 of the head portion 160. A suitable tool such as a screw driver, wrench, pliers, or the like is used to engage the proximal end portion 152 of the deployable member 136 in a rotating action to extend the threaded end portion 152 beyond the end opening 138 of the bore 134 (or bore 192 of the hex extension) to engage the internal threads 162 of the head 160 of the distal segment 120. Their actions secure the proximal and distal segments in a coupled relationship and inhibits any relative longitudinal and rotational movements between the segments.

As discussed above, the proximal segment 130 is securably coupled to the distal segment 120 as a distraction device while being anchored onto the bone structure. After the need for the distraction has been met, the proximal segment 130 is detached from the distal segment 120. From the coupled configuration, the elongated body 132 is held stationary and, using segment 152, the deployable member 136 is rotated in a direction opposite to that which was used to effect its coupling to the internal threads 162 of the head 160. This rotation disengages threads 150 from threads 162 of the distal segment 120. The rotation also releases the friction between the distal portion of the elongated body and the head portion of the distal segment. Detachment of the proximal and the distal segment is thus effected, leaving the latter securely implanted onto the vertebral structure, as shown in FIG. 3.

The deployable member can be retracted and stowed into the internal bore 134 of the proximal segment. For the embodiment as shown in FIG. 5, once the complemental threads 150 and 162 are disengaged, the proximal segment 130 can be dislodged with the key 170 disengaged from the receptacle 172 to separate from the distal segment 120. In a similar manner, for the embodiment shown in FIGS. 6a and 6b, once threads 150 and 162 are de-coupled, the hex extension 190 can be withdrawn from hex socket 194 of the distal segment. In this way, the use of the rotation locking means further ensures that the distal segment 120 would not be inadvertently rotated and de-coupled from the skeletal bone while rotating the deployable member 136 during detachment of the proximal and distal segments.

FIGS. 7a-7c, 8a-8c, 9a, 9b, 10a, 10b, 11, 12a, 12b illustrate other embodiments of the modular distraction screw. Since a thorough description of the device has been presented above, only the relevant design differences of the other embodiments will be described in detail.

FIG. 7a demonstrates another embodiment of the proximal segment. This embodiment employs an elongated proximal segment 130 with a smooth internal bore 134 and no internal threads. A deployable member 133 has a threaded tip 150 on its distal end and proximal segment 152 which is adapted so as to be engaged by a screw driver, wrench or the like in order effect its rotation. A flange 154 is placed immediately distal to the engageable proximal end. FIG. 7b demonstrates the assembled proximal segment wherein the outer elongated body and the deployable member are each independently rotatable from the other. FIG. 7c shows the proximal segment 130, distal segment 160 and the wrench 187. As threads 150 of the proximal segment are engaged with threads 162 of the distal segment, flange 154 limits the extension of the deployable member and applies a compressive force across the elongated element 130, thus forming a rigid distraction screw. As before, the screw is inserted into bone by application of a rotational force onto element 180 using wrench 187. Rotation may be achieved by any engageable means and is in no way limited to the hex-wrench arrangement illustrated. After completion of the bone work, the distal segment is disengaged from the proximal segment by rotation of element 152 in the direction opposite to that used for engagement while segment 130 is held stationary using element 180. Optionally, a rotation locking means can be incorporated as part of the distal tip of the proximal segment in order to ensure that the distal segment 120 does not inadvertently rotate and de-couple from the skeletal bone during distraction screw disassembly.

FIGS. 8a-8c shows another embodiment of the present invention in which a proximal/distal interface is defined by a threaded extension 157 disposed on the head portion of the distal segment. The threaded extension 157 is fitted within the complmental threaded female receptacle 156 of the proximal segment. It is understood that the head of the distal segment beneath extension member 157 may be of any geometric configuration. Further, in these or any of the other embodiments presented herein, the proximal/distal interface is not limited to the screw and screw receptacle arrangement depicted. Thus, for example, FIGS. 9a and 9b demonstrate a sprocket arrangement 159 (male member) and a complementary receptacle 143 (female member), and FIGS. 10a and 10b show a smooth male member 161 with a key which is used to engage the complementary receptacle 145. These two design arrangements demonstrate the adaptation that any engageable means can be used.

FIGS. 11a, 11b, 12a and 12b demonstrate a sprocket arrangement which permits a locking engagement with the complementary receptacle. As illustrated in FIGS. 12a and 12b, the cylindrical head 163, which is a smaller-diameter continuation of the screw shank 124, is fitted with engageable teeth 167 in the parallel plane (along the long axis of shank 124) and engageable teeth 165 in the perpendicular plane. The distal end portion of the elongated body 132 is provided with a receptacle 147 which is complimentary to the cylindrical head 163 of the distal segment 120. Receptacle 147 has a central bore and engageable teeth in both the parallel and perpendicular planes relative to the long axis of the proximal segment to accommodate and engage teeth 163 and 165 of the distal element 120.

The elongated body 132 of the proximal segment 130 has an engageable proximal end portion 181, which is adapted to be rotated, as for example, by means of a wrench 191. Similarly, the proximal segment 130 is rotatable by means of a wrench 189. With rotation, the proximal segment 130 advances along threads 119 to the receptacle 147 of the proximal segment around the cylindrical head 163 of the distal segment to produce a rigid distraction screw.

Wrench 191 is used to engage the end portion 181 of the proximal segment 132 to effect its rotation. The teeth within receptacle 147 of the proximal segment engage the complimentary teeth 165 and 167 of the distal segment, which rotates the distal segment and drive threads 111 into the underlying bone. Once the bone work has been completed, wrench 189 is used to rotate the proximal segment 130 in the direction opposite to that used during engagement causing it to retreat along threads 119. In this way, the head portion 163 can be disengaged from the receptacle 147 thus leaving the distal segment 120 attached to the bone. One of ordinary skill in the art will understand that the engageable arrangements described herein are illustrative and not restrictive, and that any engageable means may be alternatively used at any of these points of contact.

The distal segment 120 of the distraction screw 10, which remains securely affixed onto the vertebral bone, provides enhanced structural integrity of the bone by reducing the stress concentration generally expected of an empty opening in a structural member. Leaving the distal segment 120 in place further eliminates the robust bone bleeding encountered after removal of current, commercially-available distraction screws and obviates the need to fill the holes with a hemostatic agent.

The distal segment 120 can also provide a point of anchoring for a skeletal plate 30 or other prosthetic devices to adjust, align and maintain the spatial relationship(s) of adjacent bones or bony fragments during healing and fusion after surgical reconstruction, as shown in FIG. 4. Since placement of the distraction screws is performed as the first step in the surgical procedure, the anatomical landmarks required to ensure proper alignment of the plate or other prosthetic device in the desired anatomical plane are still intact.

Plate fixation using the affixed distal segment is largely similar for the many mono-axial embodiments illustrated. For simplicity, it will be described in detail for the first embodiment alone. As shown in FIG. 4, a skeletal plate 30 is mounted onto the distal segment, where head portion 160 is adapted with peripheral surface contour to fit an opening 32 of the skeletal plate. A mounting plate 212 having a tapered opening 214 centers the screw 210 in alignment and engagement with the threads 162 of the head portion. The mounting plate 212 also serves as a washer to assert the necessary force onto the skeletal plate 30 to be secured onto the bone substrate 20. In this way, the distal segment guides the placement of the plate and maximize the likelihood of correct anatomical alignment. It will also provide an additional point of attachment for the plate or device and enhances the structural integrity of bone/plate interface.

It is accepted that fusion of a specific spinal level will increase the load on the disc space immediately above and below the fused segment. Over time, the increased load will promote degeneration of the adjacent discs and may ultimately require that they be removed and the fusion extended to the adjacent bony level. In that event, the mounting plate 212 can be removed, permitting access to the distal segment 120. The proximal segment 130 and the elongated member 136 can be reattached to the distal segment 120 and, thus, reconstitute the distraction screw without removal.

A second distraction screw is placed into the bone of the new operative level and the surgical reconstruction is performed. After the necessary work, the proximal segments 130 are removed from each distraction screw, leaving distal segments 120 securely affixed to the vertebral bodies. A bone plate or device is affixed to maintain the spatial relationships of the new operative level while bone healing and fusion progress. Again, each distal segment 120 so affixed provides an additional point of attachment for the plate or device.

In other embodiments of the present invention, the distal segment incorporates a poly-axial design feature, which further facilitates the mounting of the skeletal plate 30 onto the vertebral bone. As used herein, "poly-axial" refers to the ability for the head portion of the distal segment to rotate about an axis that is other than that of the longitudinal axis of the threaded shank. This design provides a ready mechanism through which a skeletal plate may be affixed onto an implantable distal segment that has been placed into the skeletal bone at an angle other than the perpendicular. This situation arises when the degenerated bony elements have suffered significant mal-alignment, requiring that the distraction screws be placed at an angle to the bone surface in order to achieve the trajectory needed to realign the bones.

Examples of the poly-axial head design are illustrated in FIGS. 13, 14, 15*a-c*, 16*a*, 16*b*, 17 and 18. With such a feature, a poly-axial distal segment 220 incorporates a head portion 222, which generally assumes the geometric shape of a spherical segment, or cup shape, and a neck portion 224 with a narrower cross-sectional profile that tapers to the shank portion 226. A poly-axial head adapter 230 is swivelably fitted over the head portion 222. The poly-axial head adapter 230 has a ring body 232, which has an internal ring opening with a smaller internal diameter at its lower portion 234 than its upper portion thus forming a socket arrangement. The lower portion 234 also has a smooth concave external contour 236.

Poly-axial head adapter 230 is installed over the head portion 222 by way of the opening at its lower ring portion. A rotational space between the poly-axial head adapter 230 and the head portion 222 is provided to allow the poly-axial head adapter to move. This type of connection can be considered a ball joint, or socket connection, though other means for providing a connecting relationship between the poly-axial head adapter and the head portion while permitting varying degrees of rotational flexibility (swivelability) can also be adapted.

A flange 228 is located between the neck portion 224 and the shank portion 226, on which the poly-axial head adapter 230 can be rested. Flange 228 also provides as a stop when the shank 226 is inserted onto the bone structure, as well as a measure of the depth of the shank implant. A concave curvature in the lower portion of the flange 228 allows the maximum thread/bone contact and support when the distal segment 220 is affixed in an inclined angle relative to the surface of the bone 20.

Coupling of the proximal segment 130 and the distal segment 220 in this embodiment can employ any of the coupling designs described in detail for the mono-axial distal segment. These methods include, but are not limited to, the design illustrated in FIGS. 13 and 14. Once coupled, the segments will function as a unitary device. By applying a rotational force to the proximal segment 130, the threaded shank of the distal segment 226 can be advanced and secured into the underlying bone, as described for the mono-axial design.

Following the distraction work and detachment of the proximal segment from the implantable distal segment, the skeletal plate 30 can be mounted onto the implantable distal segment. As shown in FIG. 15, the adapter ring 230 is peripherally contoured for it to be fitted within an opening 32 of the skeletal plate 30.

Poly-axial head adapter 230 has an open top with internal circumferential thread 238 for receiving a mounting plate 242 with complemental threads 244. As shown in FIGS. 15, 15*a* and 15*b*, mounting plate 242 has a circular-shaped top flange 246, which is seated on the rim 34 of the opening 32 of the skeletal plate 30. After the skeletal plate 30 is mounted onto the adapter ring 230, the mounting plate 242 is threaded onto its internal thread 238, thus forming a unitary piece. Before the treads 242 and 238 are completely engaged, the skeletal plate can be tilted or rotated for it to be aligned in proper placement. Since the adapter ring 30 is swivelable in relation to the head portion 222, skeletal plate 30 can be easily manipulated to assume the desired position in relation to the bone structure despite the other than normal or vertical entry of the distal segment onto the bone structure.

After placement of the bone plate 30, the mounting plate 242 is tightened against the thread 238. The force asserted by the thread engagement draws the head adapter close to the mounting plate, which in turn closes the space between the lower portion 234 of the adapter ring and the head portion 222 and to firmly secure the head adapter onto the distal segment as well as the skeletal plate. As shown in FIG. 15a, the mounting plate has a central opening 250 into which a turning devise can be inserted to facilitate its turning. Although illustrated as a hexagonal opening into which an "Allen" wrench driver may be deployed, any engagement method consisting of a driver and complimentary receptacle can be employed.

FIGS. 16a, 16b, 17 and 18 show another variation in the poly-axial design feature. The poly-axial head adapter 310 is provided with a cap 312, which is coupled to the head adapter by means of threads 318. In assembly, screw 274 is fitted into the poly-axial head adapter 310 and cap 312 is used to engage threads 318. The screw 274 has a head portion 276 and a flat top 278. The cap 312 has a central opening 316 with internal threads 320, which is adapted to receive the threaded, rounded distal end 402 of the deployable member 136. Cap 312 may be further adapted to receive an optional rotation locking means. While the key design (opening 314) is illustrated for simplicity, it is understood that the rotation locking means may be of any engageable configuration.

After key 170 is fitted into the key opening 314, the deployable member is extended to pass through the threaded opening 316 and to push against the top surface 278 of the screw 274. As the threaded distal portion is rotated further in relation to threads 320, the force exerted by the rounded end 402 on surface 278 causes the under surface of the screw head 276 to firmly engage portion 322 of head adapter 310, forming a unitary distraction screw. With distraction screw assembly, its important that the long axis of the proximal segment 130 be the same as the long axis of screw 274, permitting uniform rotation of both segments along a common axis. In use, a rotational torque is applied to the proximal segment 130, which is translated by the key 170 to the head adapter 310 and, in turn, to screw 274. The shank rotates and engages the underling bone.

Following distraction and bony realignment, the proximal portion is detached from the poly-axial head adapter, leaving the implantable distal segment affixed to bone. The skeletal plate 30 is mounted with its opening 32 to fit over the peripherally contour of the distal segment and is manipulated to assume the desired position. The swivel action of the poly-axial head adapter permits proper placement of the skeletal plate even with angled placement of bone screw 274. A mounting plate 324 is seated on the stepped rim 34 of the opening 32 of the skeletal plate 30. It has a central opening 326 though which a mounting screw 328 can be passed to engage threads 320 of screw cap 312. As the threads are tightened, force is exerted onto surface 278 by the rounded end of screw 328 causing the under surface of the screw head 276 to firmly engage portion 322 of head adapter 310, and locking the poly-axial head portion to screw 274. The same action also effects a force on the mounting plate, bearing against the step rim 34 of the skeletal plate 30 for it to be securely anchored. For this embodiment, it is understood that a space is provided between the screw cap and the mounting plate to provide for the engagement of the poly-axial head adapter and the head portion.

From the above, it is apparent that the poly-axial design will produce a highly versatile distraction screw and can be used even with significantly mal-aligned bony structures. The ability of adapter ring 310 to rotate and swivel permit it to accommodate and orient the skeletal plate 30, thus ensuring proper alignment and correct plate fixation.

As described above, the present invention is that of a distraction screw and its use. It provides a significant design advantage over existing art by decreasing the bone stress encountered at the empty bone holes and reducing the extent of operative bleeding. The present design also provides an additional point of fixation for the implantable plate/prosthesis, maximizes the likelihood of proper plate/prosthesis alignment, and provides a ready mechanism for modular extension of the surgical reconstruction to adjacent levels at a future date. While the different embodiments of the present invention have been illustrated as consisting of a proximal and distal segment, it is understood that a modular distraction screw may be constructed from more than two components. The preceding descriptions and accompanying drawings are to be considered as illustrative and not restrictive in character.

Further understanding of the present invention, and other embodiments as described herein can be obtained through a review of the claims:

What is claimed is:

1. A distraction screw adaptable for surgical work on a mammalian bone structure, comprising:
    (a) a proximal segment having an elongated body with an internal bore extending through the length of the elongated body;
    (b) a deployable member disposed within the internal bore of the elongated body and adapted to be retractably deployed outside the internal bore wherein the deployable member has a length that is greater than a length of the elongated body such that the deployable member protrudes outside of first and second ends of the elongated body when disposed within the internal bore;
    (c) a distal segment including a head portion and a threaded shank portion and being detachably coupled to the elongated body and engageable with the proximal segment for implantation onto the bone structure, wherein the head portion of the distal segment has a height that is equal to its mean diameter; and
    a poly-axial head adapter secured to the distal segment, the poly-axial head adapter being swivelable around the axis defined by direction of the thread rotation of the shank portion, wherein the poly-axial head adapter further comprises a cap having a threaded opening to accommodate the deployable member passing therethrough for asserting a force against the distal segment and effecting the engagement between at least a portion of the head portion of the distal segment and the poly-axial head adapter.

2. The distraction screw of claim 1, wherein the deployable member is rod-shaped.

3. The distraction screw of claim 1, wherein the deployable member and the distal segment are detachably coupled by interfitting threads.

4. The distraction screw of claim 3, wherein the interfitting threads are right-hand threads.

5. The distraction screw of claim 1, wherein the deployable member and the internal bore each having interfitting threads adaptable for rotational engagement of the deployable member in relation to the elongated body to effect the disposition of the deployable member within the internal bore and its deployment outside the internal bore.

6. The distraction screw of claim 5, wherein the interfitting threads are configured at a selected location along the internal bore of the proximal segment.

7. The distraction screw of claim 6, wherein the location for the configuration of the interfitting threads of the deployable member and the internal bore is selected from the proximal end portion, the distal end portion or the entire length of the proximal segment.

8. The distraction screw of claim 1, wherein the elongated body is engageable to the distal segment in rotation for implantation of the distal segment onto the mammalian bone structure.

9. The distraction screw of claim 8, wherein the mammalian bone structure is selected from cancellous bone or cortical bone.

10. The distraction screw of claim 8, wherein the distal segment is securably affixed to the implant site.

11. The distraction screw of claim 1, wherein the threaded shank portion of the distal segment further comprises self-tapping flute.

12. The distraction screw of claim 1, wherein the threaded shank portion of the distal segment further comprises self-drilling flute.

13. The distraction screw of claim 1, wherein the head portion of the distal segment is disc-like.

14. The distraction screw of claim 13, wherein the head portion has a frustum shape.

15. The distraction screw of claim 1, which further comprises rotational-locking means to inhibit relative rotational movements between the proximal segment and the distal segment.

16. The distraction screw of claim 15, wherein the rotational-locking means includes a key disposed at the distal end portion of the proximal member and a depression formed of the distal segment to define a receptacle for receiving the key.

17. The distraction screw of claim 15, wherein the rotational-locking means includes a hex extension disposed at the distal end portion of the proximal member and a depression formed of the distal segment to define a socket for receiving the hex extension.

18. The distraction screw of claim 15, wherein the rotational-locking means includes a square-jaw clutch arrangement partially defining the proximal interface between the proximal segment and the distal segment.

19. The distraction screw of claim 15, wherein the rotational-locking means includes a spinal jaw clutch arrangement partially defining the proximal interface between the proximal segment and the distal segment.

20. The distraction screw of claim 15, wherein the rotational-locking means includes serrated tooth edges partially defining the proximal interface between the proximal segment and the distal segment.

21. The distraction screw of claim 1, wherein the proximal segment is adapted to be engaged by a tool to effect a rotational action to secure the distal segment onto the mammalian bone structure.

22. The distraction screw of claim 21, wherein the tool is selected from the group of tools consisting of a wrench, a socket, and pliers.

23. The distraction screw of claim 1, wherein the deployable member is adapted to be engaged by a tool selected from a flat head, Phillips head, square drive, hex head, and Allen head screw driver to effect a rotational action.

24. The distraction screw of claim 1, wherein at least a portion of the distal segment is constructed of a biologically adaptable or biologically compatible material.

25. The distraction screw of claim 24, wherein the biologically adaptable or biologically compatible material is selected from stainless steel, titanium, combination metallic alloys, plastics, and ceramics.

26. The distraction screw of claim 1, wherein at least a portion of the distal segment is constructed of a material selected from the group of materials consisting of osteo-conductive materials, osteo-inductive materials, and bio-active materials.

27. The distraction screw of claim 26, wherein the osteo-conductive material is a demineralized bone matrix or a hyroxyapatite.

28. The distraction screw of claim 27, wherein the osteo-inductive material is a transforming growth factor, platelet-derived growth factor or a bone-morphogenic protein.

29. The distraction screw of claim 1, wherein the distal segment being implanted onto the bone structure further defines a fixation point for a skeletal plate to be mounted onto the bone structure.

30. The distraction screw of claim 29, wherein the skeletal plate has an opening to accommodate the distal segment of the distraction screw for mounting onto the bone structure.

31. The distraction screw of claim 30, wherein the head portion of the distal segment has an external surface contour to accommodate the opening of the skeletal plate.

32. The distraction screw of claim 30, wherein the head portion of the distal segment is defined by the geometric shape of a frustum.

33. The distraction screw of claim 30, wherein the head portion of the distal segment is defined by the geometric shape of a spherical segment.

34. The distraction screw of claim 1, wherein the head portion of the distal segment is disposed in a fixed relationship with the shank portion and defining a common mono-axial relationship in the direction of the thread rotation.

35. The distraction screw of claim 1, wherein the poly-axial head adapter has a circumferential inner contour to engage at least a portion of the head portion of the distal segment.

36. The distraction screw of claim 1, wherein the poly-axial head adapter frictionally engages at least a portion of the head portion of the distal segment.

37. The distraction screw of claim 1, wherein the proximal portion has a key extension and the cap further having a key receptacle for receiving the key extension to effect rotation of the poly-axial head adapter by the proximal segment.

38. The distraction screw of claim 37, wherein the distal segment is implanted onto the bone structure with an inclined angle of affixation.

39. The distraction screw of claim 38, wherein implantation of the distal segment onto the bone structure is effected by the deployable member asserting a force against the distal segment, engaging the key in the key receptacle and turning the proximal segment in the direction of the threads on the shank portion at the location of the implantation.

40. The distraction screw of claim 39, wherein the distal segment implanted onto the bone structure and the poly-axial head adapter in engagement with the distal segment further defines a fixation point for a skeletal plate mounted onto the bone structure.

41. The distraction screw of claim 40, wherein the poly-axial head adapter further has a peripheral surface contour and the skeletal plate has an opening to accommodate the peripheral surface contour of the poly-axial head adapter.

42. A distraction screw adaptable for surgical work on a mammalian bone structure, comprising:
  (a) a proximal segment having an elongated body with an internal bore extending through the length of the elongated body;
  (b) a deployable member disposed within the internal bore of the elongated body and adapted to be retractably deployed outside the internal bore wherein the deployable member has a length that is greater than a length of the elongated body such that the deployable member protrudes outside of first and second ends of the elongated body when disposed within the internal bore;

(c) a distal segment including a head portion and a threaded shank portion and being detachably coupled to the elongated body and engageable with the proximal segment for implantation onto the bone structure; and (d) a poly-axial head adapter secured to the distal segment, the poly-axial head adapter being swivelable around the axis defined by direction of the thread rotation of the shank portion, wherein the poly-axial head adapter further comprises a cap having a threaded opening to accommodate the deployable member passing therethrough for asserting a force against the distal segment and effecting the engagement between at least a portion of the head portion of the distal segment and the poly-axial head adapter and wherein the proximal portion has a key extension and the cap further has a key receptacle for receiving the key extension to effect rotation of the poly-axial head adapter by the proximal segment.

* * * * *